United States Patent
Miyano et al.

(10) Patent No.: US 10,188,270 B2
(45) Date of Patent: Jan. 29, 2019

(54) STENT DELIVERY SYSTEM

(71) Applicant: OLYMPUS CORPORATION, Tokyo (JP)

(72) Inventors: Hiromichi Miyano, Fujisawa (JP); Toshihiro Yamagata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 149 days.

(21) Appl. No.: 15/268,546

(22) Filed: Sep. 17, 2016

(65) Prior Publication Data

US 2017/0000318 A1 Jan. 5, 2017

Related U.S. Application Data

(63) Continuation of application No. PCT/JP2015/052948, filed on Feb. 3, 2015.

(30) Foreign Application Priority Data

Mar. 26, 2014 (JP) .................................. 2014-063515

(51) Int. Cl.
*A61F 2/95* (2013.01)
*A61B 1/00* (2006.01)
(Continued)

(52) U.S. Cl.
CPC ............ *A61B 1/00133* (2013.01); *A61F 2/94* (2013.01); *A61F 2/95* (2013.01); *A61F 2/966* (2013.01);
(Continued)

(58) Field of Classification Search
CPC ........ A61B 1/00133; A61F 2/94; A61F 2/966; A61F 2/95; A61F 2230/0069;
(Continued)

(56) References Cited

U.S. PATENT DOCUMENTS

| | | | |
|---|---|---|---|
| 5,282,860 A | 2/1994 | Matsuno et al. | |
| 2005/0043706 A1* | 2/2005 | Eaton | .................. A61K 9/0024 604/500 |

(Continued)

FOREIGN PATENT DOCUMENTS

| | | |
|---|---|---|
| CN | 103281964 A | 9/2013 |
| JP | H05-192389 A | 8/1993 |

(Continued)

OTHER PUBLICATIONS

Chinese Office Action dated Mar. 29, 2017 in Chinese Patent Application No. 201580013078.X.

(Continued)

*Primary Examiner* — Darwin Erezo
*Assistant Examiner* — Erich Herbermann
(74) *Attorney, Agent, or Firm* — Scully, Scott, Murphy & Presser, P.C.

(57) ABSTRACT

A stent delivery system includes a guide catheter, a tubular stent into which the guide catheter can be inserted, and a tubular pusher catheter into which the guide catheter can be inserted and disposed nearer to a proximal end side than the stent. The pusher catheter includes a diameter expansion-suppressing part provided at a distal end part and having the same inner diameter as the stent and an intermediate part provided at a proximal end side of the diameter expansion-suppressing part and having a bending stiffness less than that of the diameter expansion-suppressing part. When the stent is pushed toward a distal end side by pushing the intermediate part of the pusher catheter toward the distal end side and bringing a distal end part of the diameter expansion-suppressing part into contact with a proximal end part of the stent, an inner diameter of the pusher catheter is prevented from expanding.

9 Claims, 7 Drawing Sheets

(51) Int. Cl.
*A61F 2/966* (2013.01)
*A61F 2/94* (2013.01)
*A61F 2/04* (2013.01)

(52) U.S. Cl.
CPC . *A61F 2002/041* (2013.01); *A61F 2230/0069* (2013.01)

(58) Field of Classification Search
CPC ...... A61F 2002/041; A61F 2/92; A61F 2/958; A61F 2/945
See application file for complete search history.

(56) References Cited

U.S. PATENT DOCUMENTS

| | | | |
|---|---|---|---|
| 2005/0085892 A1* | 4/2005 | Goto | A61F 2/94 623/1.12 |
| 2007/0293929 A1 | 12/2007 | Aoba et al. | |
| 2008/0004685 A1 | 1/2008 | Seemann et al. | |
| 2008/0114435 A1* | 5/2008 | Bowe | A61F 2/95 623/1.11 |
| 2008/0132906 A1 | 6/2008 | Rasmussen | |
| 2011/0295265 A1 | 12/2011 | Hollett et al. | |

FOREIGN PATENT DOCUMENTS

| | | |
|---|---|---|
| JP | 2000-152985 A | 6/2000 |
| JP | 2007-236632 A | 9/2007 |
| JP | 2008-012307 A | 1/2008 |
| JP | 2010-511428 A | 4/2010 |
| JP | 2012-502746 A | 2/2012 |
| JP | 2013-518691 A | 5/2013 |
| WO | 2008/066917 A1 | 6/2008 |
| WO | 2010/033592 A1 | 3/2010 |
| WO | 2011/098911 A1 | 8/2011 |

OTHER PUBLICATIONS

International Search Report issued in International Application No. PCT/JP2015/052948 dated Apr. 21, 2015 (in English and Japanese).

\* cited by examiner

STENT DELIVERY SYSTEM

This application is a continuation application based on PCT Patent Application No. PCT/JP2015/052948, filed Feb. 3, 2015, whose priority is claimed on Japanese Patent Application No. 2014-063515, filed Mar. 26, 2014. The contents of both the PCT Patent Application and the Japanese Patent Application are incorporated herein by reference.

BACKGROUND OF THE INVENTION

Field of the Invention

The present invention relates to a stent delivery system for placing a stent in a bile duct or the like.

Description of Related Art

When a stenosis or occlusion occurs in a hollow organ of a digestive system, a respiratory system, a urinary system, a reproductive system, or the like, a stent is used in a stenosis or occluded portion to recover an inherently provided drainage function, or to secure a drainage feature. When a stent is placed at a desired position within a bile duct or the like, an operation is performed using a stent delivery system (hereinafter simply referred to as a delivery system. Hereinafter, the delivery system is assumed to include a stent). As this type of delivery system, for example, a system disclosed in Japanese Unexamined Patent Application, First Publication No. 2000-152985 is known.

The delivery system includes a guide catheter, a stent into which the guide catheter is inserted, and a pusher catheter into which the guide catheter is inserted and which is positioned closer to a hand side than the stent.

The delivery system is used as follows. A guide wire is introduced into a bile duct through a channel of an endoscope, and a distal end of the guide wire is inserted to a position beyond a stenosis portion. Next, the guide wire is covered with the guide catheter from the hand side, the guide catheter is pushed using the guide wire as a guide, and a distal end part of the guide catheter is inserted to a position beyond the stenosis portion of the bile duct.

Next, the stent is pushed by the pusher catheter, the stent is introduced into the bile duct using the guide catheter as the guide, and the stent is disposed at a position of the stenosis portion. Only the guide catheter is pulled back to the hand side in a state in which the stent is supported by touching the pusher catheter with the stent and the stent and the pusher catheter are fixed so as not to move. Thereafter, the pusher catheter is pulled back to the hand side so that the stent is placed and maintained within the stenosis portion.

SUMMARY OF THE INVENTION

According to a first aspect of the present invention, a stent delivery system includes: a guide catheter capable of being inserted into a channel of an endoscope; a stent formed in a tube shape and into which the guide catheter is capable of being inserted; and a pusher catheter formed in a tube shape and into which the guide catheter is capable of being inserted, the pusher catheter being disposed nearer to a proximal end side than the stent. The pusher catheter includes: a diameter expansion-suppressing part provided at a distal end part of the pusher catheter and having an inner diameter the same as an inner diameter of the stent; and an intermediate part provided at a proximal end side of the diameter expansion-suppressing part and having a bending stiffness less than a bending stiffness of the diameter expansion-suppressing part. When the stent is pushed toward a distal end side by pushing the intermediate part of the pusher catheter toward the distal end side and causing a distal end part of the diameter expansion-suppressing part to come into contact with a proximal end part of the stent, the diameter expansion-suppressing part prevents an inner diameter of the distal end part of the pusher catheter from expanding.

According to a second aspect of the present invention, in the stent delivery system according to the first aspect, a thickness of a tube wall of the stent in a radial direction may be the same as a thickness of a tube wall of the pusher catheter in the radial direction. A difference between the inner diameter of the stent and an outer diameter of the guide catheter may be less than or equal to 8% of the inner diameter of the stent.

According to a third aspect of the present invention, in the stent delivery system according to the second aspect, the diameter expansion-suppressing part and the intermediate part may be made of the same type of material to be mixed at different mixing ratios.

According to a fourth aspect of the present invention, in the stent delivery system according to the third aspect, the pusher catheter may be formed of a monolayer tube. The stent may be formed of a multilayer tube obtained by stacking different materials in the radial direction.

According to a fifth aspect of the present invention, in the stent delivery system according to the first aspect, the bending stiffness of the diameter expansion-suppressing part may be greater than a bending stiffness of the stent.

According to a sixth aspect of the present invention, in the stent delivery system according to the fifth aspect, the bending stiffness of the intermediate part may be less than the bending stiffness of the stent.

According to a seventh aspect of the present invention, in the stent delivery system according to the sixth aspect, the bending stiffness of the diameter expansion-suppressing part may be less than or equal to 200% of the bending stiffness of the stent. The bending stiffness of the intermediate part may be greater than or equal to 50% of the bending stiffness of the stent.

DETAILED DESCRIPTION OF THE INVENTION

Hereinafter, an embodiment of a delivery system according to the present invention will be described with reference to FIGS. 1 to 11.

Figure 1:
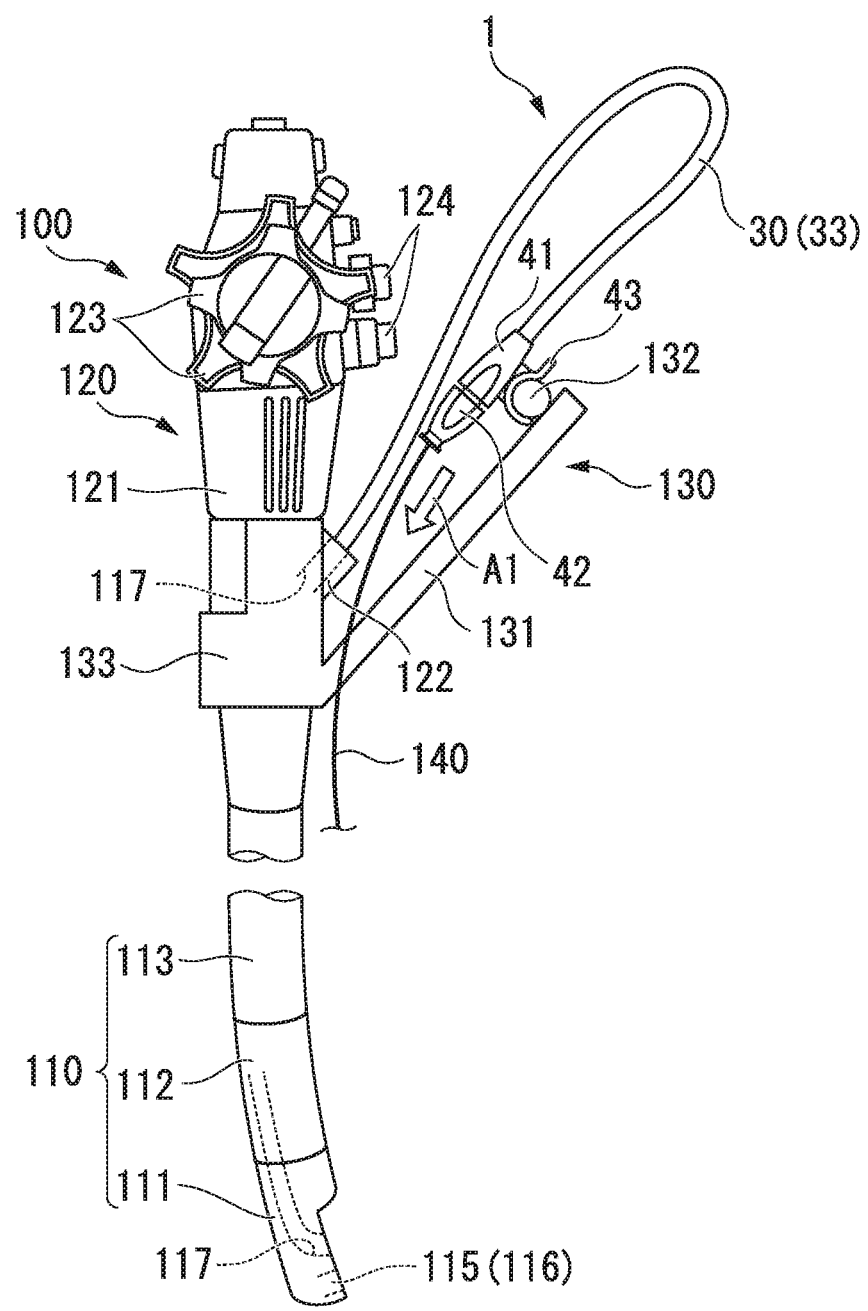
FIG. 1 is an overall diagram illustrating a state in which a delivery system according to an embodiment of the present invention is attached to an endoscope.

Hereinafter, first, an endoscope used together with the present delivery system will be described. As illustrated in FIG. 1, an endoscope 100 is a so-called flexible side view type endoscope and includes an elongated insertion part 110 and a manipulation part 120 provided at a proximal end part of the insertion part 110.

The insertion part 110 includes a distal end rigid part 111 provided at a distal end part, a bent part 112 attached to a proximal end side of the distal end rigid part 111 and capable of being operated to be bent, and a flexible tube part 113 attached to the proximal end side of the bent part 112. A distal end part of a light guide 115 and an imaging unit 116 having a charge-coupled device (CCD) (not illustrated) are provided on a side surface of the distal end rigid part 111 in an externally exposed state. In the insertion part 110, a channel 117 for inserting an endoscopic treatment tool such as a delivery system 1 is formed. The distal end part of the channel 117 is opened in the above-mentioned side surface of the distal end rigid part 111. The proximal end part of the channel 117 extends to the manipulation part 120. A raising base (not illustrated) is provided at a part corresponding to the distal end rigid part 111 of the channel 117. The proximal end part of the raising base is supported to be rotatable on the distal end rigid part 111. A raising base manipulation wire (not illustrated) fixed to the distal end part of the raising base is inserted into the insertion part 110 and extends to the proximal end side.

Although not illustrated, a plurality of bending pieces arranged side by side in a longitudinal direction of the insertion part 110 and mutually connected to be swingable are embedded in the bent part 112. A distal end part of a bending piece manipulation wire is fixed to a bending piece arranged at a most distal end side among the bending pieces. The bending piece manipulation wire extends to the proximal end side through the inside of the insertion part 110.

A forceps port 122 is provided at a distal end side of a manipulation part main body 121 constituting the manipulation part 120. The proximal end part of the channel 117 is opened in the forceps port 122. A lever (not illustrated) for manipulating the above-mentioned raising base manipulation wire, a knob 123 for manipulating the bending piece manipulation wire, and a switch 124 for manipulating a light source (not illustrated), a monitor (not illustrated), the above-mentioned imaging unit 116, or the like are provided on the proximal end side of the manipulation part main body 121. The bent part 112 can be bent in a desired direction by manipulating the knob 123.

An endoscope adapter 130 is installed to be detachable at the manipulation part 120. The endoscope adapter 130 includes a rod-shaped adapter main body 131, a cylindrical treatment tool-fixing part 132 engaged with the delivery system 1 and disposed at one end part of the adapter main body 131, and an endoscope-fixing part 133 disposed at the other end part of the adapter main body 131 substantially molded in a semi-cylindrical shape and having a segmented portion.

Figure 2:
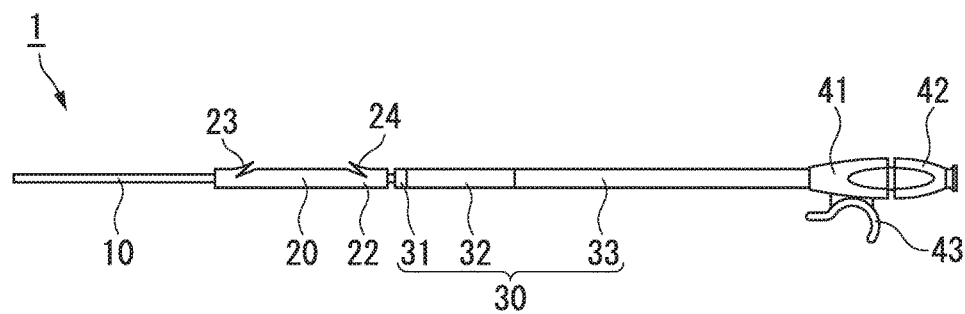
FIG. 2 is a side view of the delivery system.
Figure 3:
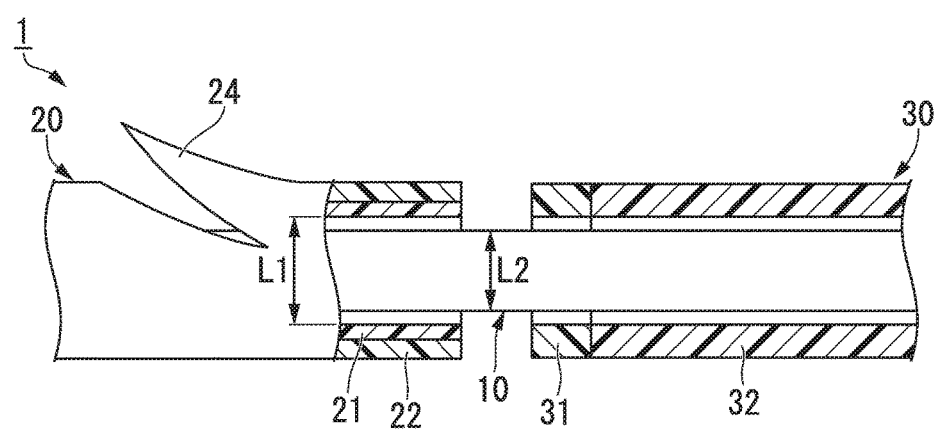
FIG. 3 is a side view illustrating a fractured part of a main part in FIG. 2.

Next, the delivery system 1 according to the present embodiment will be described. As illustrated in FIGS. 2 and 3, the delivery system 1 includes a guide catheter 10 capable of being inserted into the channel 117 of the endoscope 100, a stent 20 formed in a tube shape and into which the guide catheter 10 can be inserted, and a pusher catheter 30 formed in a tube shape, into which the guide catheter 10 can be inserted, and arranged closer to the proximal end side than the stent 20.

Here, a cantilever stiffness test for measuring bending stiffness will be described when components of the delivery system 1 are described. The guide catheter 10, the stent 20, and the pusher catheter 30 mentioned above are used as a tubular sample S1 illustrated in FIG. 4. In a state in which a distal end side of the sample S1 protrudes by 5 mm or more, an outer peripheral surface of a proximal end side of the sample S1 is grasped and supported by a clamp R1. The sample S1 is arranged to be parallel to a horizontal plane. At this time, a cylindrical core body R2 is inserted into a conduit of the sample S1 in a range in which the sample S1 is grasped by the clamp R1 in a longitudinal direction of the sample S1. An outer diameter of the core body R2 is substantially the same as an inner diameter of the conduit of the sample S1.

Figure 5:
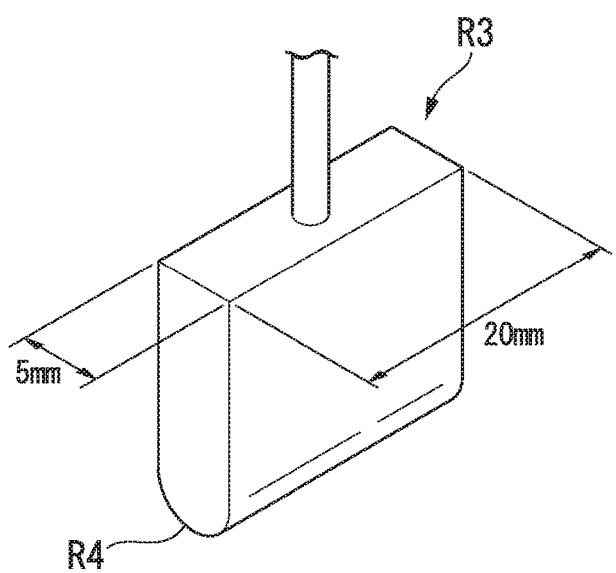
FIG. 5 is an explanatory diagram of an attachment used in the cantilever stiffness test.

In FIG. 5, an attachment R3 used to exert a load on the sample S1 is illustrated. The attachment R3 is formed in a plate shape having a width of 20 mm and a thickness of 5 mm. A contact surface R4 of the attachment R3 in contact with the sample S1 is formed in a curved shape having a curvature radius of 2.5 mm so that a bending load for the sample S1 is not concentrated on one point.

Figure 4:
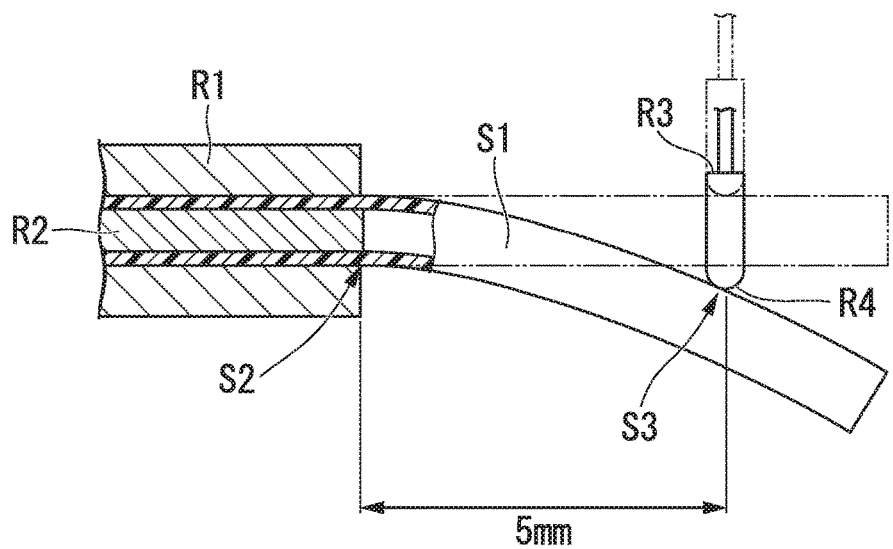
FIG. 4 is a diagram illustrating a method of a cantilever stiffness test.

As illustrated in FIG. 4, a position of the outer peripheral surface of the sample S1 corresponding to a distal end surface of the clamp R1 is designated as a fulcrum S2, and the attachment R3 is set such that the contact surface R4 of the attachment R3 abuts a force point S3, which is a position of the outer peripheral surface separated 5 mm along a horizontal plane from the fulcrum S2, from above. A measurement device (not illustrated) depresses the attachment R3 5 mm in a vertically downward direction at a speed of 10 mm/minute while concurrently measuring a deflection when the attachment R3 is depressed and a reaction force that the attachment R3 receives from the sample S1. A maximum reaction force received while the attachment R3 is depressed 5 mm is measured, and the measured maximum reaction force is the bending stiffness of the sample S1. The bending stiffness in the present description is measured by the cantilever stiffness test.

Also, a bending stiffness ratio is defined by the following Formula (1).

$$((\text{Bending stiffness of diameter expansion-suppressing part or intermediate part})/\text{Bending stiffness of stent})\times 100(\%) \quad (1)$$

Next, components of the delivery system 1 will be described. As the guide catheter 10, a guide catheter having a well-known configuration formed of a tubular resin having biocompatibility such as polypropylene or polyethylene can be used.

The stent 20 may be formed of a multilayer tube in which an inside layer 21 and an outside layer 22 formed of resin materials in a tube shape are radially stacked. FIG. 3 illustrates the stent 20 having a two-layer structure, wherein the outside layer 22 covers an outer peripheral surface of the inside layer 21. The inside layer 21 and the outside layer 22 are formed of different materials. For example, it is possible to form the inside layer 21 of perfluoroalkoxy alkane (PFA) and form the outside layer 22 of a polyurethane-based elastomer resin. Thereby, flexibility can be imparted to the stent 20 having low invasiveness while the stent 20 is placed, and good sliding properties (delivery system operability) can be imparted to the stent 20 and the guide catheter 10. Flaps 23 and 24 illustrated in FIGS. 2 and 3 are formed in the distal end part and the proximal end part of the stent 20, respectively. The flap 23 is formed to open outward in a radial direction toward the proximal end side. The flap 24 is formed to open outward in the radial direction toward the distal end side. In this example, the flaps 23 and 24 are formed by cutting and raising the outside layer 22 and the inside layer 21.

Also, the stent 20 may be formed of a monolayer tube made of a resin material, and a reinforcing layer such as a blade layer or a coil layer may be disposed within the monolayer tube or the multilayer tube. The stent 20 is arranged to be able to slide on the distal end side of the guide catheter 10.

The pusher catheter 30 includes a diameter expansion-suppressing part 31 provided at the distal end part of the pusher catheter 30, an intermediate part 32 provided at a proximal end side of the diameter expansion-suppressing part 31, and a proximal-end-side rigid part 33 provided at a proximal end side of the intermediate part 32. That is, the distal end part of the pusher catheter 30 is constituted of the diameter expansion-suppressing part 31, a proximal end side closer than the diameter expansion-suppressing part 31 in the pusher catheter 30 is constituted of the intermediate part 32, and a proximal end side closer than the intermediate part 32 in the pusher catheter 30 is constituted of a proximal-end-side rigid part 33. Each of the diameter expansion-suppressing part 31, the intermediate part 32, and the proximal-end-side rigid part 33 is formed of a monolayer tube in a tube shape. In this example, inner diameters of the diameter expansion-suppressing part 31, the intermediate part 32, and the proximal-end-side rigid part 33 are the same as one another, and outer diameters of the diameter expansion-suppressing part 31, the intermediate part 32, and the proximal-end-side rigid part 33 are the same as one another.

The inner diameter of the diameter expansion-suppressing part 31 and the inner diameter of the stent 20 are substantially the same (they can also be the same). A wall thickness of the stent 20 and a wall thickness of the pusher catheter 30 are substantially the same (they can also be the same). That is, the stent 20, the diameter expansion-suppressing part 31, the intermediate part 32, and the proximal-end-side rigid part 33 have substantially the same wall thickness. Here, in the present description, the "wall thickness" is a dimension in a radial direction of a tube wall in a structure formed in a tube shape. A length of the diameter expansion-suppressing part 31 in an axial direction is appropriately set in a range in which insertion into the channel 117 is possible (it is not caught (not stacked) in the channel 117) when the bent part 112 of the endoscope 100 is bent. When the length of the diameter expansion-suppressing part 31 is long, it is difficult to push the delivery system 1 into the channel 117 formed in the bent part 112 which is bent. It is preferable that the length of the diameter expansion-suppressing part 31 be less than 10 mm, and it is more preferable that the length of the diameter expansion-suppressing part 31 be about 2 mm. A bending stiffness of the intermediate part 32 is less than a bending stiffness of the diameter expansion-suppressing part 31.

A method of configuring the diameter expansion-suppressing part 31 may be any method in which processing such as physical processing or chemical processing is enabled in a predetermined dimension. Physical processing includes, for example, a method of forming the diameter expansion-suppressing part 31 and the intermediate part 32 by a junction of the tube (a welding), disposing a metallic pipe within the diameter expansion-suppressing part 31, or performing insert molding to configure the diameter expansion-suppressing part 31. Alternatively, chemical processing includes a method of expressing a molecular cross-linked structure of a thermoplastic resin by electron beam processing.

When the diameter expansion-suppressing part 31 is formed in the junction of the tube, it is preferable to mix a filler with the resin material and mold the filler mixed with the resin material as a compound (resin kneading) material. As the diameter expansion-suppressing part 31 is configured as described above, because it is easy to adjust mechanical properties such as surface hardness, bending stiffness, and extensibility to appropriate values, it is possible to manufacture the diameter expansion-suppressing part 31 suitable for a use environment of the delivery system 1.

The resin material to be used in the diameter expansion-suppressing part 31 is represented by the following thermoplastic resin. However, any thermoplastic resin may be used as long as a desired mechanical property is provided.

General purpose resins such as olefin-based resins such as polypropylene and polyethylene, a copolymer resin thereof, a polyester-based resin (polyethylene terephthalate (PET) or the like), and polyvinyl alcohol (PVA)

Engineering resins such as polyamide-based resins, polyester-based resins (PBT or the like), a fluorine-based resin (e.g., PTFE, PVDF, PFA, FEP, ETFE), and polyether ether ketone (PEEK)

Various types of elastomer resins (a polystyrene-based resin, a polyolefin-based resin, a polyurethane-based resin, a polyester-based resin, a polyamide-based resin, a polyvinyl chloride-based resin, etc.), a silicone-containing resin, a polyurethane-based resin, etc.

The filler is not limited to the resin materials and is mixed with the resin material to adjust mechanical properties or chemical properties of the diameter expansion-suppressing part 31. Also, the filler may not be mixed with the resin material. Organic fillers among the fillers can include an ultraviolet (UV) inhibitor, a cellulose nanofiber, etc. Inorganic fillers among the fillers can include metals (carbon black, tungsten, etc.), metal compounds (calcium carbonate, barium sulfate, diamond-like carbon (DLC), etc.), metal oxides (titanium oxide, silica, or the like), and minerals (talc, clay, etc.).

Mechanical properties are imparted to the diameter expansion-suppressing part 31 by, for example, making a tube configuration having a multilayer tube in which reinforcing layers such as a coil and a blade are arranged as means having mechanical properties such as rigidity. Also, in order to secure bonding strength between the diameter expansion-suppressing part 31 and the intermediate part 32, it is desirable to further increase an amount of a welded resin, and a monolayer tube in which only a resin material serving as a component is preferably used as the diameter expansion-suppressing part 31 or the intermediate part 32.

The pusher catheter 30 may be configured by manufacturing and welding a set of the diameter expansion-suppressing part 31 and the intermediate part 32 and a set of the intermediate part 32 and the proximal-end-side rigid part 33 with the same material. In this case, because the types of materials mixed in the diameter expansion-suppressing part 31, the proximal-end-side rigid part 33, and the intermediate part 32 are the same, the compatibility during welding is good and the bonding strength is improved. When the diameter expansion-suppressing part 31, the intermediate part 32, and the proximal-end-side rigid part 33 are not manufactured and configured with the same type of material as described above, it is necessary to perform surface modification, binder arrangement, or the like to achieve required bonding strength. A manufacturing cost of the pusher catheter may increase by increasing the number of processing steps. By configuring the pusher catheter 30 using a tube junction, processing is easily performed in predetermined dimensions without requiring large-scale equipment (an initial investment) when the pusher catheter 30 is manufactured.

It is preferable that the types of mixed materials of the diameter expansion-suppressing part 31 and the intermediate part 32 be the same as each other and mixing ratios of the materials be different from each other. Thereby, the bonding strength during weld bonding is maintained and an adjustment to a predetermined bending stiffness is easy. For example, a relatively soft elastomer resin and a relatively rigid thermoplastic resin are used as the above-mentioned resin material so that the bending stiffness of the intermediate part 32 is less than the bending stiffness of the diameter expansion-suppressing part 31. The elastomer resin and the thermoplastic resin are mixed in the diameter expansion-suppressing part 31 and the intermediate part 32, and the mixing ratio of the thermoplastic resin in the diameter expansion-suppressing part 31 is greater than the mixing ratio of the thermoplastic resin in the intermediate part 32. The proximal-end-side rigid part 33 is formed of the same material as that of the diameter expansion-suppressing part 31. That is, the bending stiffness of the proximal-end-side rigid part 33 is equal to the bending stiffness of the diameter expansion-suppressing part 31.

Figure 6:
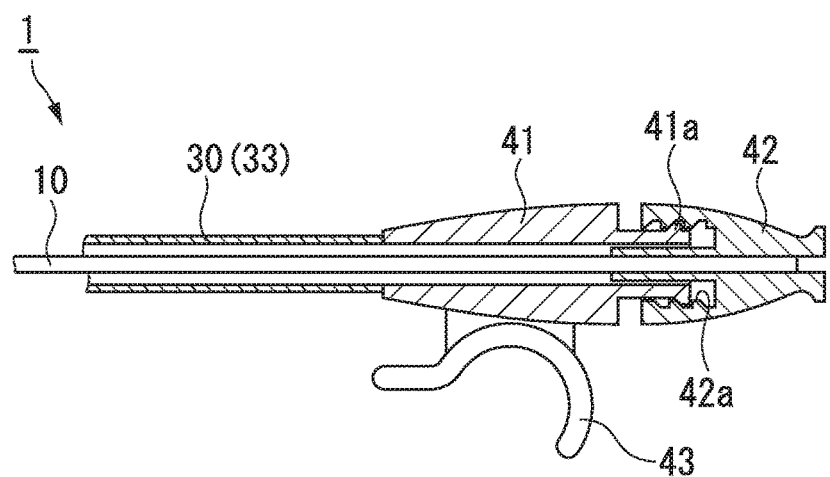
FIG. 6 is a cross-sectional view of a side surface of a manipulation portion of the delivery system.

As illustrated in FIG. 6, a pusher cap 41 is attached to the proximal end part of the proximal-end-side rigid part 33 of the pusher catheter 30. A male screw part 41a is formed at the proximal end part of the pusher cap 41. A hook 43 with an elastically deformable C shape is attached to the pusher cap 41. In the hook 43, a slanting distal end side is opened in a side view. When the hook 43 is attached to the treatment tool-fixing part 132 of the endoscope adapter 130, the hook 43 slides around the treatment tool-fixing part 132. A cap 42 is attached to the proximal end part of the guide catheter 10. In a distal end part of the cap 42, a female screw part 42a which is screwed onto the male screw part 41a is formed.

Next, an operation of the delivery system 1 configured as described above will be described as an example of when the stent 20 is placed within a bile duct.

When the light source is operated by manipulating the switch 124 of the manipulation part 120, illuminating light emitted from the light source is guided by the light guide 115 and illuminates a periphery of the distal end rigid part 111 of the insertion part 110. An image of the periphery of the distal end rigid part 111 of the insertion part 110 captured by the imaging unit 116 is displayed on a monitor. The user inserts the insertion part 110 of the endoscope 100 into a body cavity of a patient through a natural orifice of a mouth or the like while viewing the image displayed on the monitor. At this time, the knob 123 is optionally manipulated to bend the bent part 112.

Figure 7:
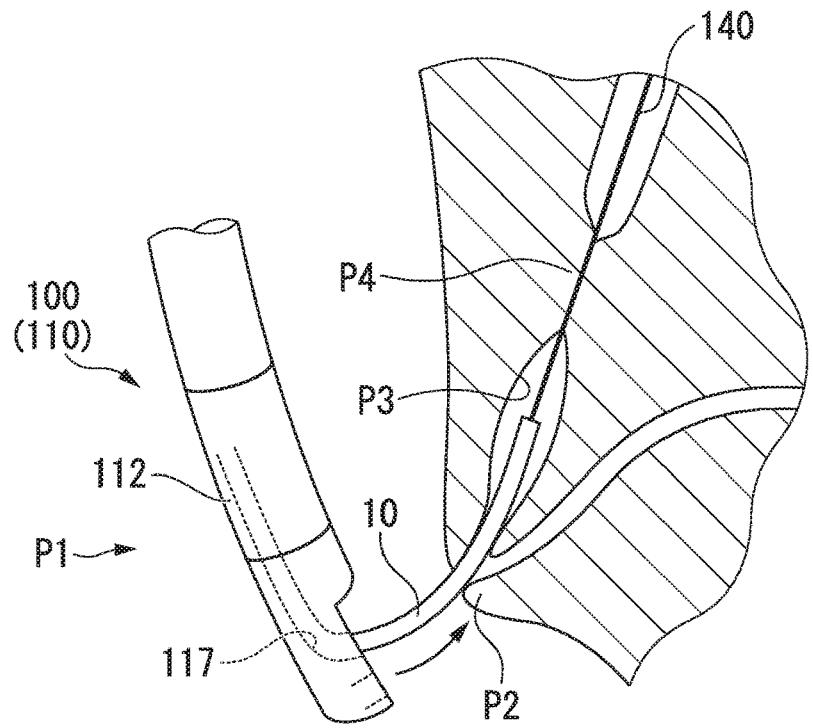
FIG. 7 is a diagram illustrating an operation of the delivery system.

As illustrated in FIG. 7, the distal end part of the insertion part 110 moves into the vicinity of a duodenal papilla P2 through a duodenum P1. An opening of the distal end part of the channel 117 opposes the duodenal papilla P2. The guide wire 140 is inserted into the forceps port 122 of the endoscope 100, and the guide wire 140 protruding from the distal end part of the channel 117 is inserted into a stenosis portion P4 of a bile duct P3. At this time, the raising base is appropriately manipulated to adjust the direction of the guide wire 140 protruding from the opening of the distal end part of the channel 117.

Next, as illustrated in FIG. 1, the endoscope-fixing part 133 of the endoscope adapter 130 is mounted at a predetermined position of the manipulation part 120 of the endoscope 100. The stent 20 on the distal end side of the guide catheter 10 and the pusher catheter 30 on the proximal end side thereof are arranged to be able to slide in an outer peripheral part of the guide catheter 10. The distal end part of the guide catheter 10 is inserted along the proximal end side end part of the guide wire 140 protruding from the forceps port 122. Parts of the distal end sides of the stent 20 and the pusher catheter 30 are inserted into the channel 117.

In the vicinity of the forceps port 122, the guide catheter 10 and the pusher catheter 30 are folded back in the middle, and the hook 43 is attached to the treatment tool-fixing part 132 of the endoscope adapter 130. While the hook 43 rotates on the treatment tool-fixing part 132, the cap 42 opposes the forceps port 122 and adjustment is performed so that the guide catheter 10 and the pusher catheter 30 are substantially parallel to the guide wire 140 protruding from the cap 42.

In this state, the proximal-end-side rigid part 33 of the pusher catheter 30 and the guide wire 140 are grasped together and move in a direction of an arrow A1 in the drawing. At this time, a length in which the guide catheter 10 and the pusher catheter 30 are inserted into the channel 117 is the same as a length in which the guide wire 140 is extracted from the cap 42. Accordingly, by repeating this operation, as illustrated in FIG. 7, the guide catheter 10 and the pusher catheter 30 are inserted into the channel 117 in a state in which a distal end position of the guide wire 140 is constantly maintained, and a distal end of the guide catheter 10 is inserted to a desired position. By causing a force to act on the proximal-end-side rigid part 33, the force is effectively delivered to the proximal end side of the pusher catheter 30.

Figure 8:
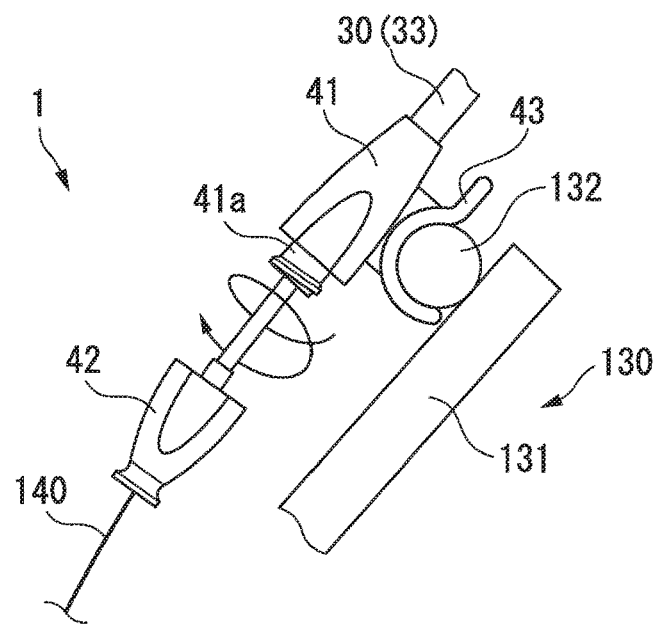
FIG. 8 is a diagram illustrating an operation of the delivery system.
Figure 9:
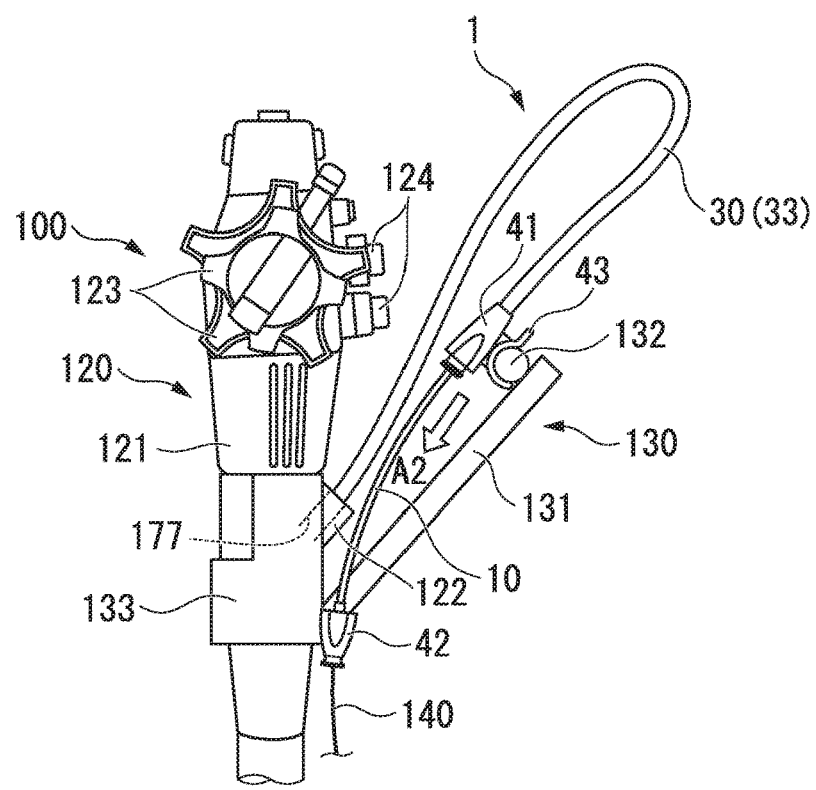
FIG. 9 is a diagram illustrating an operation of the delivery system.

Next, as illustrated in FIG. 8, the cap 42 rotates with respect to the pusher cap 41, and the cap 42 is removed from the pusher cap 41. As illustrated in FIG. 9, the guide catheter 10 is extracted from the pusher cap 41 while the cap 42 is grasped, and the guide catheter 10 protruding from the pusher cap 41 and the pusher catheter 30 are arranged to be substantially parallel in the vicinity of the forceps port 122.

The proximal-end-side rigid part 33 of the pusher catheter 30 and the guide catheter 10 are grasped together and move in a direction of an arrow A2 of FIG. 9. At this time, a length in which the pusher catheter 30 is inserted into the channel 117 is the same as a length in which the guide catheter 10 and the guide wire 140 are extracted from the pusher cap 41.

Figure 10:
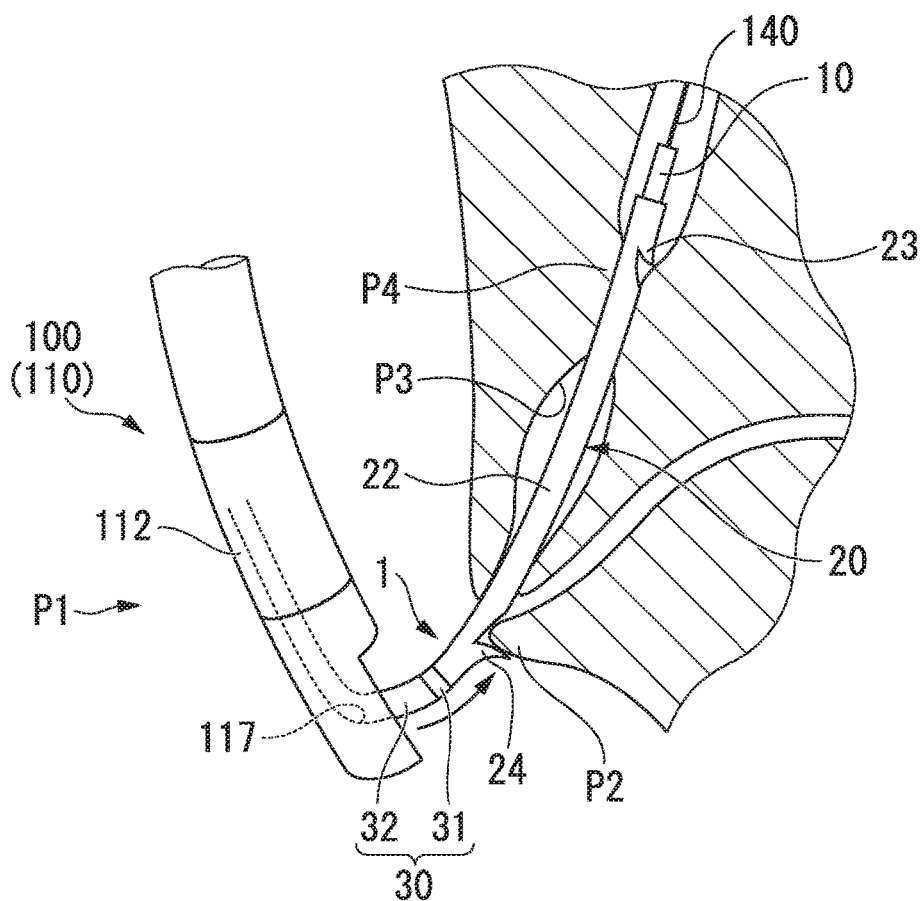
FIG. 10 is a diagram illustrating an operation of the delivery system.

As illustrated in FIG. 10, the intermediate part 32 is moved (pushed) to the distal end side via the proximal-end-side rigid part 33 with respect to the guide catheter 10 and the distal end part of the diameter expansion-suppressing part 31 abuts the proximal end part of the stent 20 so that the stent 20 is pushed toward the distal end side. Around the outer peripheral surface of the guide catheter 10, the stent 20 and the pusher catheter 30 slide to the distal end side. Because the bending stiffness of the diameter expansion-suppressing part 31 is greater than the bending stiffness of the intermediate part 32, the diameter expansion-suppressing part 31 prevents the inner diameter of the distal end part of the pusher catheter 30 from expanding (increasing) compared to the inner diameter of the intermediate part 32. Thereby, the proximal end surface of the stent 20 and the distal end surface of the diameter expansion-suppressing part 31 reliably come into contact with each other, and the force acting on the diameter expansion-suppressing part 31 is efficiently delivered to the stent 20. When the intermediate part 32 of the pusher catheter 30 is arranged within the channel 117 formed in the bent part 112, the bending of the bent part 112 is easily maintained because the bending stiffness of the intermediate part 32 is relatively small.

By repeating the above-mentioned operation, as illustrated in FIG. 10, the pusher catheter 30 is inserted into the channel 117 in a state in which the distal end positions of the guide catheter 10 and the guide wire 140 are constantly held, and the stent 20 is inserted to a position at which the flap 23 of the stent 20 is locked on a liver side of the stenosis portion P4 and the flap 24 of the stent 20 is locked on the duodenal papilla P2. Thereafter, the guide catheter 10, the pusher catheter 30, and the guide wire 140 are pulled out from the inside of the bile duct P3 and extracted from the channel 117 of the endoscope 100 so that the stent 20 is placed (released).

Figure 11:
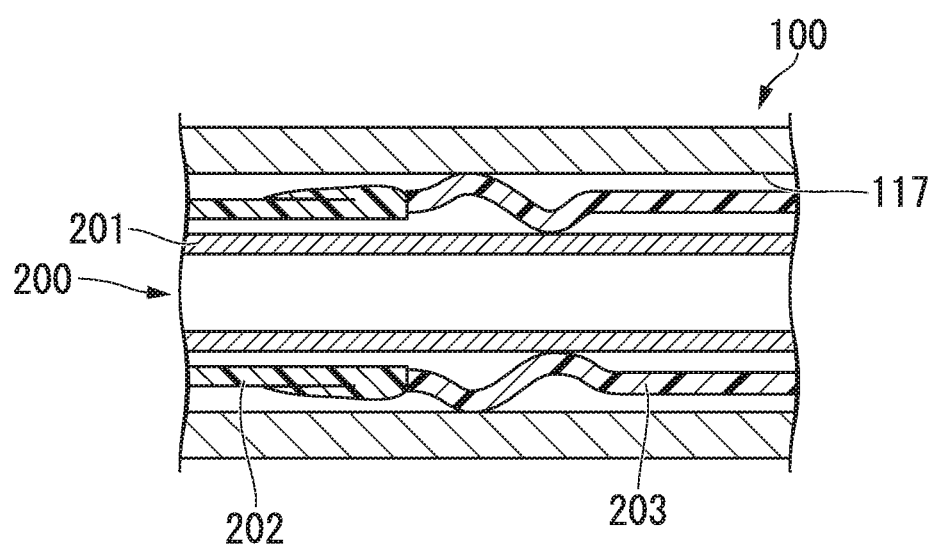
FIG. 11 is a cross-sectional view illustrating an operation of a conventional delivery system.

In FIG. 11, a state in which a conventional delivery system 200 is inserted into the channel 117 of the endoscope 100 is illustrated. The delivery system 200 includes a guide catheter 201, and a stent 202 and a pusher catheter 203 into which the guide catheter 201 can be inserted. When the bent part 112 of the endoscope 100 is bent and the stent 202 is unlikely to be moved to the distal end side, a distal end part of the pusher catheter 203 may be deformed in a bellows shape when the stent 202 is pushed if the pusher catheter 203 is moved to the distal end side relative to the guide catheter 201. In this case, the distal end part of the pusher catheter 203 having an expanded diameter strongly comes into contact with the inner peripheral surface of the channel 117. A frictional force between the inner peripheral surface of the channel 117 and the distal end part of the pusher catheter 203 increases, a force necessary to push the stent 202 or the pusher catheter 203 increases, and operability of a user deteriorates. When the delivery system is inserted into the channel of the endoscope, the outer diameter of the delivery system is limited to be less than the inner diameter of the channel. In the placement of the stent, the pusher catheter formed in a tube shape performs an operation of pushing the stent formed in a tube shape while being guided by the guide catheter.

According to the delivery system 1 of the present embodiment, the pusher catheter 30 includes the diameter expansion-suppressing part 31 provided at the distal end part and the intermediate part 32 provided at the proximal end side of the diameter expansion-suppressing part 31. Thus, when the distal end part of the diameter expansion-suppressing part 31 is allowed to abut the proximal end part of the stent 20 by pushing the intermediate part 32 to the guide catheter 10, the stent 20 is pushed toward the distal end side in a state in which the diameter expansion-suppressing part 31 prevents the inner diameter of the distal end part of the pusher catheter 30 from expanding. Therefore, when the pusher catheter 30 pushes the stent 20, it is possible to reliably release the stent 20 from the pusher catheter 30 after pushing the stent 20 without covering and storing the distal end part of the pusher catheter 30 in the proximal end part of the stent 20 and radially making a bulge at an outside and an inside simultaneously.

When there is a large difference between the wall thickness of the stent 20 and the wall thickness of the pusher catheter 30, axial deviation is likely to occur between the stent 20 and the pusher catheter 30, particularly, from the opening of the distal end part of the channel 117 to the duodenal papilla P2. Thus, it is impossible to uniformly deliver a pushing force to the stent 20 and placement of the stent 20 is difficult. Because the stent 20 and the pusher catheter 30 have substantially the same wall thickness, it is possible to prevent the axial deviation between the stent 20 and the pusher catheter 30 from occurring.

When the wall thickness of the pusher catheter 30 is thin, the force acting on the pusher catheter 30 is efficiently delivered to the stent 20 by providing the diameter expansion-suppressing part 31 at the distal end part of the pusher catheter 30, and an effect of delivering and maintaining the force from the pusher catheter 30 to the stent 20 tends to increase. Consequently, by providing the diameter expansion-suppressing part 31 at the distal end part of the pusher catheter 30, it is possible to thin the wall thickness of the pusher catheter 30 and set a wide variation of dimensions of the pusher catheter 30. Because the proximal-end-side rigid part 33 is provided at the proximal end side of the intermediate part 32 in the pusher catheter 30, the force acting on the proximal-end-side rigid part 33 can be further effectively delivered to the distal end side of the pusher catheter 30.

In the present embodiment, it is possible to variously deform a configuration of the delivery system 1 as will be described below.

As illustrated in FIG. 3, a difference (a clearance) between an inner diameter L1 of the stent 20 and an outer diameter L2 of the guide catheter 10 may be less than or equal to 8% (0.08 times) of the inner diameter L1 of the stent 20. When the above-mentioned clearance is too large, axial deviation occurs between the stent 20 and the guide catheter 10 or the pusher catheter 30, and the force pushing the pusher catheter 30 is not effectively delivered to the stent 20 (force delivery efficiency deteriorates). Particularly, when a stent having a thin wall thickness and a small bending stiffness (bending deformation is likely to occur) is placed, the stent is likely to be bent in an operation of placing the stent. Because the occurrence of frictional resistance within the channel 117 is prevented when the stent is bent, it is necessary to make bending the stent difficult by reducing a clearance.

From the study by the inventors so far, it can be confirmed that the above-mentioned axial deviation occurs and operability during placement of the stent deteriorates when a clearance design equivalent to that of an existing product (a clearance of about 22% with respect to an internal diameter of the stent) is made in the above-mentioned stent in which the wall thickness is thin. By setting the clearance to a value less than or equal to 8% of the inner diameter L1 of the stent 20, it is possible to suppress the axial deviation between the stent 20 and the pusher catheter 30 and favorably deliver the force for pushing the stent 20.

Also, in the following Formula (2), a clearance ratio is specified.

$$\{(L1-L2)/L1\} \times 100 (\%) \qquad (2)$$

In this modified example, a clearance ratio of the delivery system 1 may be less than or equal to 8%. Also, the clearance ratio of the delivery system 1 is greater than 0%.

The bending stillness of the diameter expansion-suppressing part 31 of the pusher catheter 30 may be greater than the bending stiffness of the stent 20. In general, a degree of deformation between the proximal end part of the stent and the distal end part of the pusher catheter decreases as the bending stiffness of each portion increases. Also, the degree of deformation that is mentioned here indicates a dimensional variation amount of the tube shape in the radial direction. When the bending stiffness of the diameter expansion-suppressing part 31 is greater than the bending stiffness of the stent 20, the diameter expansion-suppressing part 31 that is the distal end part of the pusher catheter 30 can push (place) the stent 20 without being deformed before the proximal end part of the stent 20. However, the following problems occur when the bending stiffness of the diameter expansion-suppressing part 31 is excessively large depending on the length of the diameter expansion-suppressing part 31 in the axial direction. That is, when the diameter expansion-suppressing part 31 passes through the inside of the channel 117 formed in the bent part 112 which is bent, a hooked feeling (a stacked feeling) occurs between the inner peripheral surface of the channel 117 and the diameter expansion-suppressing part 31 because the diameter expansion-suppressing part 31 is unlikely to be deformed. In the worst case, the inner peripheral surface of the channel 117 is likely to be damaged.

From the study by the inventors so far, it is confirmed that the stent 20 is favorably pushed into the channel 117 if the bending stiffness of the diameter expansion-suppressing part 31 is less than or equal to 200% of the bending stiffness of the stent 20 when the pusher catheter 30 passes through the inside of the channel 117 of the bent part 112 in a bent shape adapted to a use environment.

The bending stiffness of the intermediate part 32 of the pusher catheter 30 may be less than the bending stiffness of the stent 20. When the bending stiffness of the intermediate part 32 is greater than the bending stiffness of the stent 20, a reaction force that the intermediate part 32 receives from the inner peripheral surface of the channel 117 increases when the stent 20 passes through the inside of the channel 117 of the bent part 112 in the bent shape. A following capability of the delivery system 1 within the channel 117 deteriorates and force delivery efficiency for the stent 20 deteriorates. When the bending stiffness of the intermediate part 32 is less than the bending stiffness of the stent 20, the above-mentioned following capability of the delivery system 1 within the channel 117 is improved.

However, when the bending stiffness of the intermediate part 32 is excessively less than the bending stiffness of the stent 20, the following problem occurs. That is, before a necessary push force when the stent 20 breaks through the stenosis portion P4 is delivered to the stent 20, deformation such as a kink due to stress concentration in which the bending stiffness is small with respect to the reaction force of the pusher catheter 30 delivered from the stent 20 is likely to occur. Thereby, the original delivery function is not shown and quality function deterioration is caused. From the study by the inventors so far, it can be confirmed that a good delivery function is shown when the bending stiffness of the intermediate part 32 of the pusher catheter 30 is greater than or equal to 50% of the bending stiffness of the stent 20.

While an embodiment of the present invention has been described above with reference to the drawings, specific configurations are not limited to the embodiment, and changes, combinations, and deletions of the configurations, etc. can be included without departing from the spirit and scope of the present invention.

For example, in the above-mentioned embodiment, the pusher catheter 30 includes the diameter expansion-suppressing part 31, the intermediate part 32, and the proximal-end-side rigid part 33. However, the pusher catheter 30 may be configured without including the proximal-end-side rigid part 33.

The pusher catheter 30 is formed of a monolayer tube, but the pusher catheter may be formed of a multilayer tube. A reinforcing layer may be internally disposed.

EXAMPLES

An example of the present invention will be described in further detail through a specific example hereinafter, but the present invention is not limited to the following example.

(Configuration of Members)

Stent: the stent had a layer configuration of an inner layer (PFA)/a reinforcing layer (a coil)/an external layer (polyurethane) and had an inner diameter of 2.75 mm and an outer diameter of 3.2 mm.

Guide catheter: the guide catheter was made of a PFA tube and a distal end part was formed in a tapered shape which narrowed toward the distal end side. An outer diameter of a stent mount portion in which the stent was disposed was 2.6 mm.

Pusher Catheter:

Diameter expansion-suppressing part: the diameter expansion-suppressing part was subjected to tube molding in a compound material of polypropylene (Rockwell hardness (R-scale): 80), a styrene-based elastomer (durometer A hardness: 90), and barium sulfate (particle size distribution 1 to 100 μm (micrometers): cumulative frequency 80% of 1 μm to 10 μm) at a mixing ratio of 79:5:16. The diameter expansion-suppressing part was joined to an intermediate part by tube welding based on heating of a heater. The diameter expansion-suppressing part had an inner diameter of 2.75 mm and an outer diameter of 3.3 mm.

Intermediate part: the intermediate part was subjected to tube molding in a compound material of polypropylene (Rockwell hardness (R-scale): 80), a styrene-based elastomer (durometer A hardness: 90), and barium sulfate (particle size distribution 1 to 100 μm (micrometers): cumulative frequency 80% of 1 μm to 10 μm) at a mixing ratio of 54:29:17. The intermediate part was joined to the diameter expansion-suppressing part and a proximal-end-side rigid part by tube welding based on heating of a heater. The intermediate part had an inner diameter of 2.75 mm and an outer diameter of 3.3 mm. Proximal-end-side rigid part: the proximal-end-side rigid part used the same tube as the diameter expansion-suppressing part.

(Results of Measuring Members)

Bending Stiffness:

The stent had a bending stiffness of 7.2N.

Pusher Catheter

The diameter expansion-suppressing part and the proximal-end-side rigid part had a bending stiffness of 8.8N and the intermediate part had a bending stiffness of 5.7N.

Clearance ratio between the guide catheter and the stent: 5.8%

The bending stiffness of the diameter expansion-suppressing part was greater than the bending stiffness of the stent, and a bending stiffness ratio of the diameter expansion-suppressing part (when the numerator of the above-mentioned Formula (1) is the bending stiffness of the diameter expansion-suppressing part) was 122%.

The bending stiffness of the intermediate part was less than the bending stiffness of the stent, and a bending stiffness ratio of the intermediate part (when the numerator of the above-mentioned Formula (1) is the bending stiffness of the intermediate part) was 79%.

Through the above configuration, a delivery system capable of maintaining a moderate force delivery effect and reliably releasing and placing a stent is provided.

The present invention is limited only by the appended claims without being limited by the above description.

What is claimed is:

1. A stent delivery system comprising:
a guide catheter formed in a tube shape;
a stent formed in a tube shape and into which the guide catheter is inserted; and a pusher catheter formed in a tube shape and into which the guide catheter is inserted, the pusher catheter being disposed proximally relative to the stent, wherein the pusher catheter includes:

an intermediate part having a distal end part and a proximal end part; and a diameter expansion-suppressing part joined to the distal end part of the intermediate part, the diameter expansion-suppressing part having a bending stiffness greater than a bending stiffness of the intermediate part and having an inner diameter the same as an inner diameter of the stent;

an outer diameter of the diameter expansion-suppressing part is the same as an outer diameter of the intermediate part, the diameter expansion-suppressing part and the intermediate part comprise a mixture of at least a first material and a second material respectively, a mixing ratio of an amount of the first material and an amount of the second material of the diameter expansion-suppressing part being different from a mixing ratio of an amount of the first material and an amount of the second material of the intermediate part, and wherein, when the stent is pushed toward a distal end side by pushing the intermediate part of the pusher catheter toward the distal end side and causing a distal end part of the diameter expansion-suppressing part to come into contact with a proximal end part of the stent, the diameter expansion-suppressing part prevents an inner diameter of the distal end part of the pusher catheter from expanding.

2. The stent delivery system according to claim 1, wherein a thickness of a tube wall of the stent in a radial direction is the same as a thickness of a tube wall of the pusher catheter in the radial direction, and wherein a difference between the inner diameter of the stent and an outer diameter of the guide catheter is less than or equal to 8% of the inner diameter of the stent.

3. The stent delivery system according to claim 1, wherein the pusher catheter is formed of a monolayer tube, and wherein the stent is formed of a multilayer tube obtained by stacking different materials in a radial direction.

4. The stent delivery system according to claim 1, wherein the bending stiffness of the diameter expansion-suppressing part is greater than a bending stiffness of the stent.

5. The stent delivery system according to claim 4, wherein the bending stiffness of the intermediate part is less than the bending stiffness of the stent.

6. The stent delivery system according to claim 5, wherein the bending stiffness of the diameter expansion-suppressing part is less than or equal to 200% of the bending stiffness of the stent, and wherein the bending stiffness of the intermediate part is greater than or equal to 50% of the bending stiffness of the stent.

7. The stent delivery system according to claim 1, wherein at least one of the first material and the second material is thermoplastic resin.

8. The stent delivery system according to claim 1, wherein the first material is an elastomer resin, the second material is a thermoplastic resin, the mixing ratio of the amount of the thermoplastic resin relative to the elastomer resin in the diameter expansion-suppressing part is greater than the mixing ratio of the amount of the thermoplastic resin relative to the elastomer resin in the intermediate part.

9. The stent delivery system according to claim 1, wherein a length of the diameter expansion-suppressing part in a longitudinal axis direction is set to be shorter than a length of the stent in a longitudinal axis direction.

\* \* \* \* \*